(12) United States Patent
Cabezas

(10) Patent No.: US 8,730,024 B1
(45) Date of Patent: May 20, 2014

(54) UNIVERSAL REMOVABLE FUEL TANK INDICATOR

(76) Inventor: Carlos H. Cabezas, Worcester, MA (US)

( * ) Notice: Subject to any disclaimer, the term of this patent is extended or adjusted under 35 U.S.C. 154(b) by 280 days.

(21) Appl. No.: 13/415,029

(22) Filed: Mar. 8, 2012

(51) Int. Cl.
*A61L 9/12* (2006.01)
*G09F 3/04* (2006.01)
*G09F 7/06* (2006.01)
*G09F 9/302* (2006.01)
*G08B 5/00* (2006.01)

(52) U.S. Cl.
USPC ............ 340/457; 40/124.06; 40/419; 40/643; 116/307; 116/325; 141/94; 220/86.2; 239/59; 340/439; 340/450.2; D23/368

(58) Field of Classification Search
CPC ............. A61L 9/03; A61L 9/12; A61L 9/042; A61L 9/048; A61L 9/122; A61L 2209/12; B60H 3/00; B60H 3/0007; B60H 3/0021; B60H 3/0028; B60H 3/0616; Y10S 261/88; B60K 11/00; B60K 15/04; B60K 35/00; B60K 2001/0461; B60S 5/02; B67D 2007/0423; F02B 77/08
USPC ......... 340/425.5, 426.15, 426.22, 439, 450.2, 340/457; 239/34, 44, 57, 58, 59, 60; 422/5, 422/123, 124; D23/366, 367, 368; 220/86.2, 746; 137/587; 141/94; 280/834; 454/119; 116/2, 29, 30, 34 B, 116/47, 52, 209, 306, 307, 325, 326; 40/124.06, 419, 588, 593, 643, 644, 40/649
See application file for complete search history.

(56) References Cited

U.S. PATENT DOCUMENTS

| | | | |
|---|---|---|---|
| 2,573,625 A | 10/1951 | Swart | |
| 4,038,935 A * | 8/1977 | Margiloff | 116/35 R |
| 4,523,870 A * | 6/1985 | Spector | 454/157 |
| D309,902 S | 8/1990 | Schneider | |
| D350,156 S | 8/1994 | Adiv | |
| 5,422,078 A * | 6/1995 | Colon | 422/123 |
| D361,791 S | 8/1995 | Klatz | |
| D375,527 S | 11/1996 | Keogh | |
| 5,707,110 A * | 1/1998 | Campbell et al. | 297/344.1 |
| D396,064 S | 7/1998 | Beebe | |
| D422,315 S | 4/2000 | Bosack | |
| 6,103,201 A | 8/2000 | Green | |
| 6,764,656 B1 | 7/2004 | Matulevich | |
| D527,811 S | 9/2006 | Scott | |
| 8,197,761 B1 * | 6/2012 | Miller-Larry | 422/125 |
| 2006/0196965 A1 * | 9/2006 | Christianson et al. | 239/60 |
| 2011/0013109 A1 * | 1/2011 | Bryan | 349/58 |
| 2013/0056549 A1 * | 3/2013 | Dobler et al. | 239/53 |

* cited by examiner

*Primary Examiner* — Benjamin C Lee
*Assistant Examiner* — Stephen Burgdorf

(57) ABSTRACT

A removable fuel tank indicator having a housing, wherein the housing is removable and universal to all automobiles and wherein the housing attaches to an automobile connection point located within the interior of the automobile; a removable arm temporarily attached to the housing, wherein the removable arm signals which side of the automobile a fuel tank is located; a means for attaching the housing to the automobile connection point wherein the automobile connection point is located within the interior of the automobile and said connection point is capable of attaching to the housing; the fragrance cartridge adapted for insertion into the opening and locking into the cavity of the housing, wherein where the cartridge is properly inserted into the opening and cavity of the housing.

12 Claims, 4 Drawing Sheets

(ISO View)

(ISO View)

(Exploded View)

(Front View)

(Back View)

(Side View)

UNIVERSAL REMOVABLE FUEL TANK INDICATOR

BACKGROUND OF THE INVENTION

The present invention is related to devices and gadgets located in the interior of an automobile for assisting the automobile driver with operation of the automobile.

SUMMARY

The present invention features a universal and removable fuel tank indicator for the interior of an automobile. In some embodiments, the fuel tank indicator comprises a removable arm for indicating which side of an automobile a fuel tank is located, an air freshener component, and a means for attaching the fuel tank indicator to a an automobile vent.

Currently, automobile drivers struggle with the ever-continuing problem of remembering where the fuel tank is located on their respective automobiles. While some newer models of automobiles are designed with fuel tank indicators, thousands of automobiles currently provide no way for an automobile driver to remember whether the fuel tank is located on the left or right side of the automobile. Consequently, automobile drivers struggle with backing up turning around at re-fueling stations when the wrong side of the automobile is aligned adjacent to the fuel source.

When automobile drivers have to reposition their automobiles at fuel service stations, there is increased risk for accidents and a decrease in safety especially during busy hours.

As such, there is a need for a universal fuel tank indicator, a gadget that is removable and compatible with all vehicles and which signals to an automobile driver where the fuel tank is located.

In some embodiments, the present invention further comprises an air-freshener component, which provides fresh air in a variety of fragrances, thereby adding further utility to that already provided by the signaling of the fuel tank.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
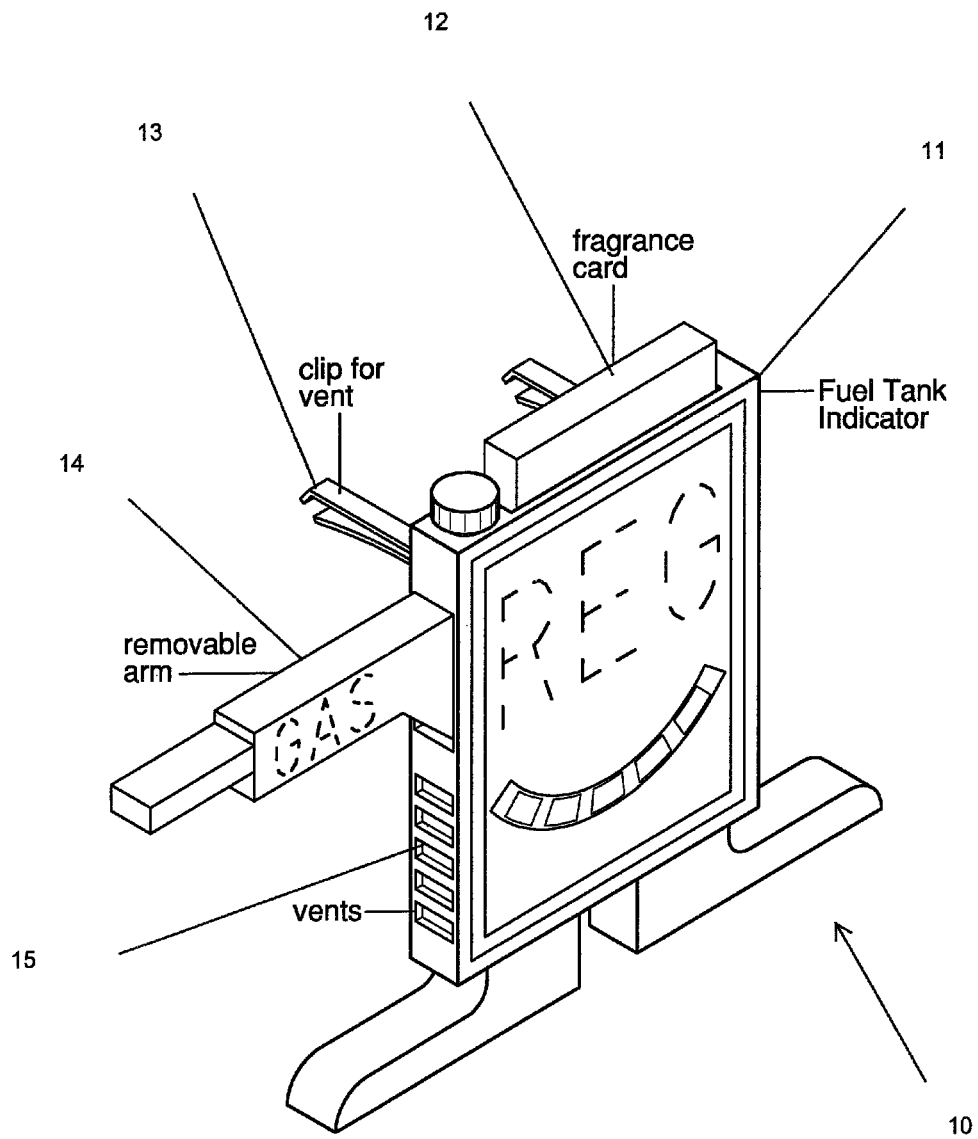
FIG. 1 is an isometric view of the of the present invention.
Figure 2:
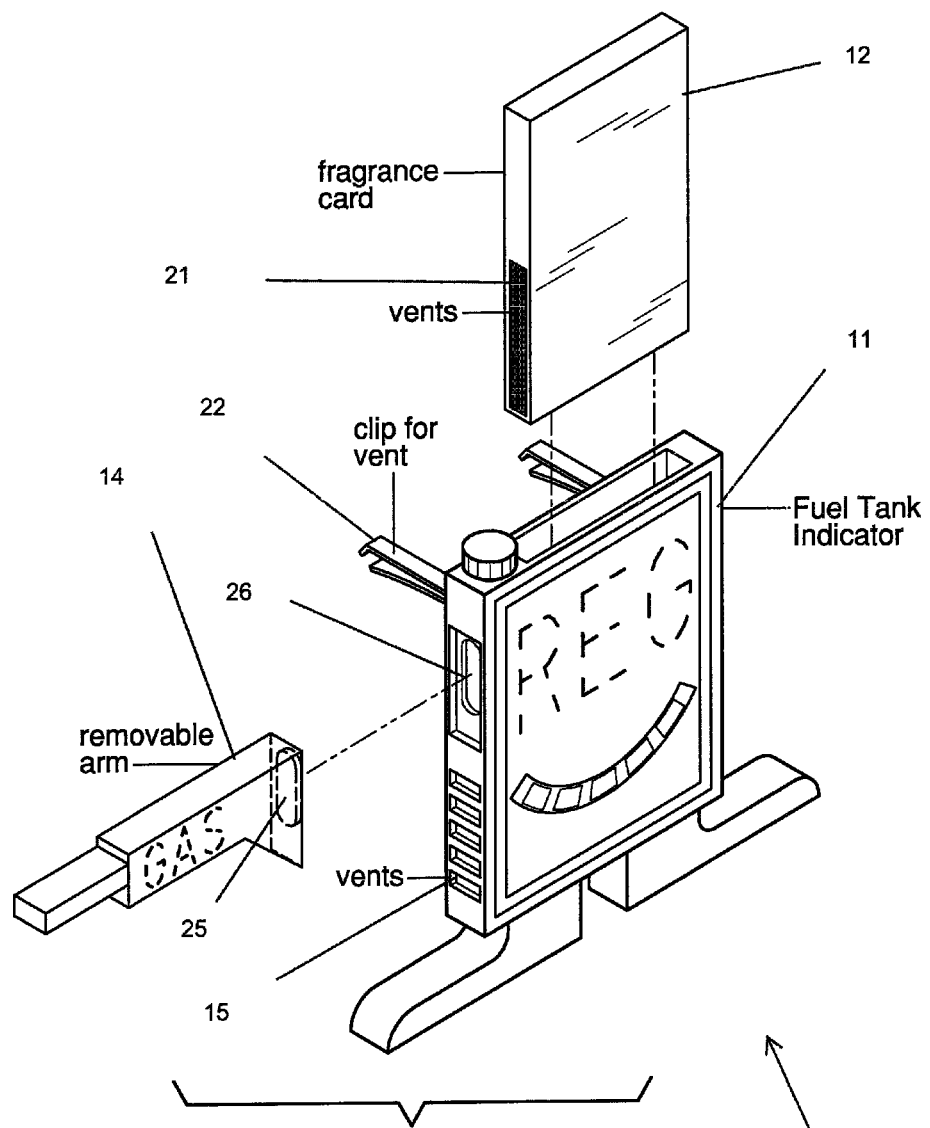
FIG. 2 is an exploded view of the of the present invention.
Figure 3:
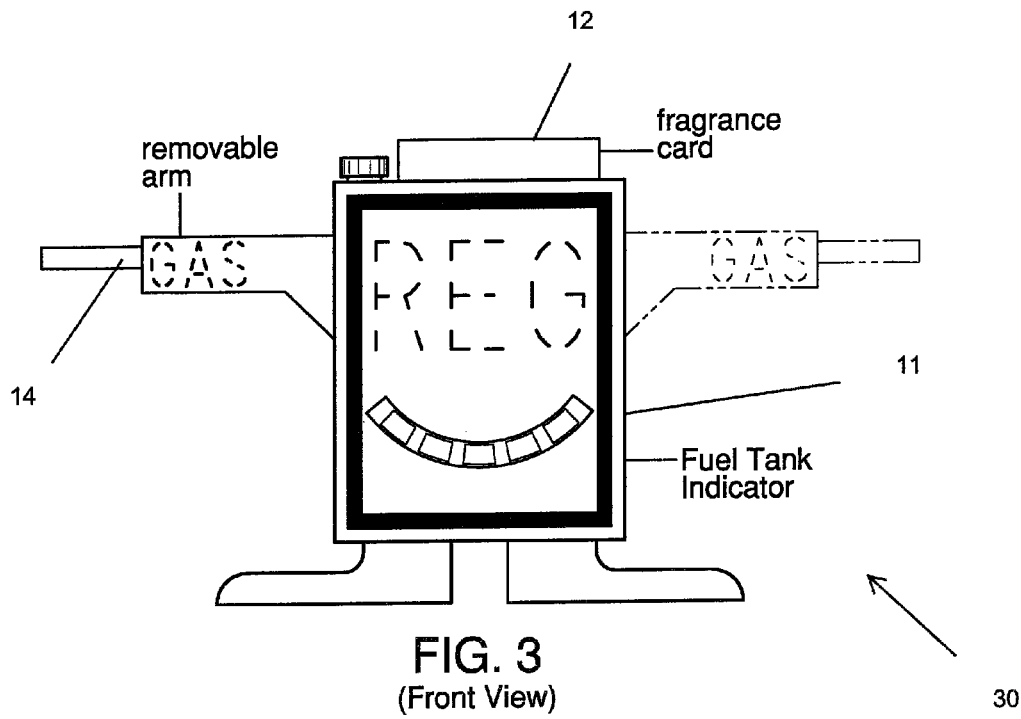
FIG. 3 is a front view of the present invention.
Figure 4:
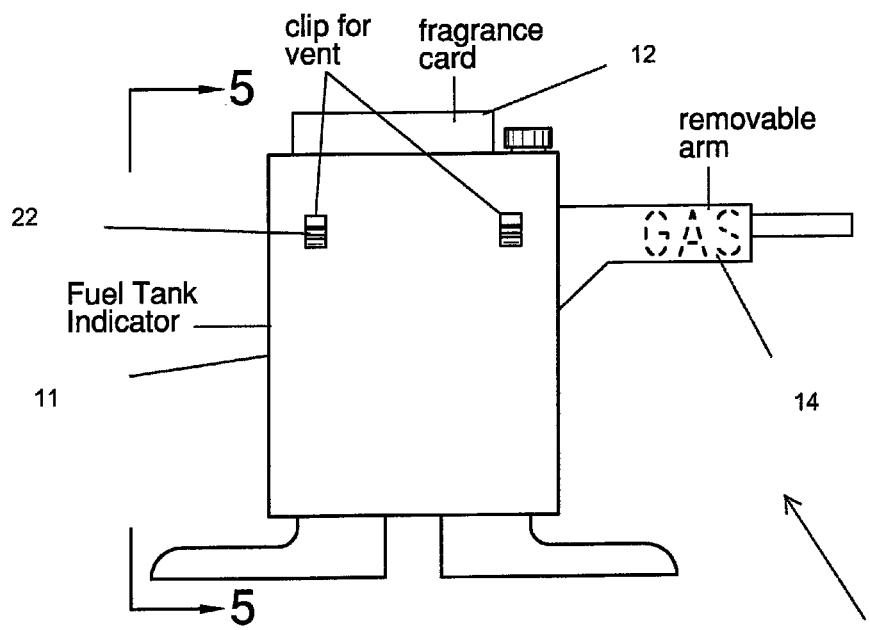
FIG. 4 is a back view of the present invention.
Figure 5:
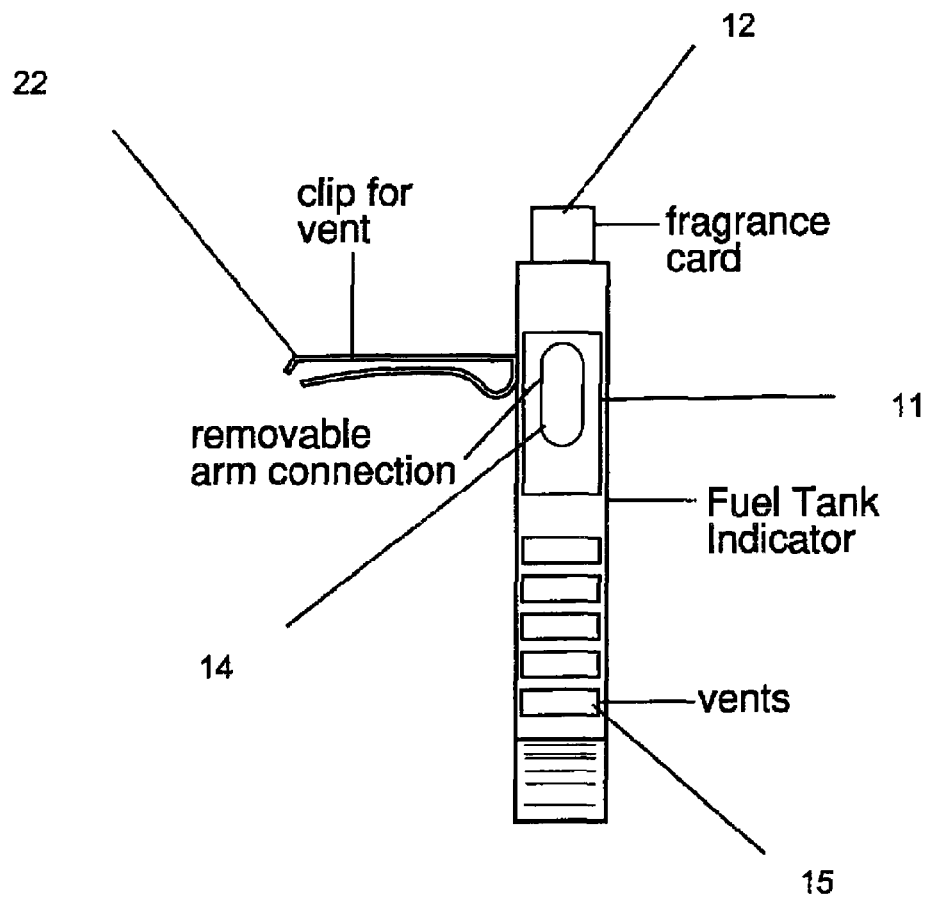
FIG. 5 is a side view of the present invention.
Figure 5:

Referring now to FIG. 1-5, the present invention features, in some embodiments, a removable fuel tank indicator [10], effective in assisting an automobile driver with refueling an automobile wherein the fuel tank indicator [10] assists the driver in obtaining proper alignment of an automobile and a fuel source. The fuel tank indicator [10] can comprise the following components.

First, a housing [11], the housing [11] having a first and second side, a first connection point [26] disposed on the first side, a second connection point [26] disposed on the second side, the housing [11] having a top opening and cavity configured for insertion of a fragrance cartridge [12], the housing [11] having a first housing vent [15] on the first side and a second housing vent [15] on the second side, wherein the housing [11] is removable and universal to all automobiles and wherein the housing [11] attaches to an automobile connection point located within the interior of the automobile.

Second, a removable arm [14] temporarily attached to the housing [11], the removable arm [14] having a complimentary connection point [25] for attachment to the first connection point [26] of the first side of the housing [11] or the second connection point [26] of the second side of the housing [11], wherein the removable arm [14] signals which side of the automobile a fuel tank is located.

Third, a means [22] for attaching the housing to the automobile connection point wherein the automobile connection point is located within the interior of the automobile and said connection point is capable of attaching to the housing [11].

Fourth, the fragrance cartridge [12], primarily for use with an automobile vent supplying a flow of air, said fragrance cartridge [12] adapted for insertion into the opening and locking into the cavity of the housing [11], the fragrance cartridge [12] further comprising a first cartridge vent [21] disposed on a first side of the cartridge [12], and a second cartridge vent [21] disposed on a second side of the cartridge [12], wherein where the cartridge is properly [12] inserted into the opening and cavity of the housing [11], the first housing vent [15] and the first cartridge vent are in alignment and the second housing vent [15] and the second cartridge vent [21] are in alignment.

In some embodiments, the fuel tank indicator [10] is universal and removable, and said fuel tank indicator [10] signals the automobile driver as to the location of a fuel tank for the automobile thereby enabling the automobile driver to align the automobile adjacent to the fuel source for efficient and safe refueling of the automobile.

It is believed that the present invention provides great utility by signaling to automobile drivers where the fuel tank is located on an automobile, thereby eliminating wasted time, and reducing risk of accidents at fuel stations caused when the automobile driver parks the automobile on the wrong side of the fuel source and needs to reposition the automobile.

In some embodiments, the present invention is portable and universal in that it can be positioned in any automobile, and in any portion of the automobile so long as there exists at that portion a connecting point capable of creating a connection with the claimed means [22] for attaching the housing.

In some embodiments, the means [22] for attaching the housing merely comprises a set of metal clips.

It would be understood by one skilled in the art that the means [22] for attaching the housing can comprise a variety of connecting means, such as glue, Velcro, wood clips, metal clips, plastic clips or other means capable of creating a temporary attachment to a surface.

In some embodiments, the removable arm, which serves the purpose of signaling to the automobile driver as to where the fuel tank is located, can be replaced by a digital signal component. As set forth in the relevant claims, the digital signal component can be a digital and electronic system for signaling to the automobile driver where the fuel tank is located and can, in some embodiments, replace the non-electronic removable arm component.

It would be understood by one skilled in the art, that the connection point [26] for the housing and the complimentary connection point for the removable arm [25] could comprise male and female slots, pressure mounts, or any other means of simple and temporary attachment and connection.

As used herein, the term "about" refers to plus or minus 10% of the referenced number.

As used herein, the term "about" refers to plus or minus 10% of the referenced number. For example, an embodiment wherein the device is about 10 inches in length includes a device that is between 9 and 11 inches in length.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

The invention claimed is:

1. A removable fuel tank indicator, effective in assisting an automobile driver with refueling an automobile wherein the removable fuel tank indicator assists the driver in obtaining proper alignment of an automobile and a fuel source, the removable fuel tank indicator comprising:
   a. a housing, the housing having a first and second side, a first connection point disposed on the first side, a second connection point disposed on the second side, the housing having a top opening and cavity configured for insertion of a fragrance cartridge, the housing having a first housing vent on the first side and a second housing vent on the second side, wherein the housing is removable and universal to all automobiles and wherein the housing attaches to an automobile connection point located within the interior of the automobile;
   b. a removable arm temporarily attached to the housing, the removable arm having a complimentary connection point for attachment to the first connection point of the first side of the housing or the second connection point of the second side of the housing, wherein the removable arm signals which side of the automobile a fuel tank is located;
   c. a means for attaching the housing to the automobile connection point wherein the automobile connection point is located within the interior of the automobile and said connection point is capable of attaching to the housing;
   d. the fragrance cartridge for use with an automobile vent supplying a flow of air, said fragrance cartridge adapted for insertion into the top opening and locking into the cavity of the housing, the fragrance cartridge further comprising a first fragrance cartridge vent disposed on a first side of the fragrance cartridge, and a second fragrance cartridge vent disposed on a second side of the fragrance cartridge, wherein where the fragrance cartridge is properly inserted into the top opening and cavity of the housing, the first housing vent and the first fragrance cartridge vent are in alignment and the second housing vent and the second fragrance cartridge vent are in alignment;

wherein the removable fuel tank indicator is universal and removable, and wherein said removable fuel tank indicator signals the automobile driver as to the location of a fuel tank for the automobile, thereby enabling the automobile driver to align the automobile adjacent to the fuel source for efficient and safe refueling of the automobile.

2. The removable fuel tank indicator of claim 1, wherein the automobile connection point is the automobile vent; and the means for attaching the removable fuel tank indicator to the automobile vent comprises two clips, fixedly attached to an upper rear portion of the removable fuel tank indicator.

3. The removable fuel tank indicator of claim 2, wherein the two clips further comprise metal, plastic, or wood.

4. The removable fuel tank indicator of claim 1, wherein the automobile connection point is the automobile vent; and the means for attaching the housing to the automobile vent comprises a plurality of flexible clips extending from the rear portion of the housing and being spaced apart from one another.

5. The removable fuel tank indicator of claim 1 wherein the interior of the fragrance cartridge is comprised of scent-bearing material.

6. The removable fuel tank indicator of claim 1 wherein the automobile vent includes at least one louver.

7. The removable fuel tank indicator of claim 1, wherein the automobile connection point comprises an automobile vent component.

8. The removable fuel tank indicator of claim 7 wherein the automobile vent component includes at least one louver.

9. The removable fuel tank indicator claim 1, wherein the fragrance cartridge is comprised of scent-bearing material.

10. The removable fuel tank indicator of claim 1 wherein the housing has a bottom side, and further comprises a pair of decorative legs affixed to the bottom side of the housing.

11. The removable fuel tank indicator of claim 1 wherein the housing further comprises a face side, and wherein a decorative downward facing arch is disposed on the bottom portion of the face side of the housing, and the letters "REG" are inscribed on the upper portion of the face side of the housing.

12. A removable fuel tank indicator effective in assisting an automobile driver with refueling an automobile wherein the removable fuel tank indicator assists the driver in obtaining proper alignment of an automobile and a fuel source, the removable fuel tank indicator comprising:
   a. a housing, the housing having a first and second side, the housing having a top opening and cavity configured for insertion of a fragrance cartridge, the housing having a first housing vent on the first side and a second housing vent on the second side, wherein the housing is removable and universal to all automobiles and wherein the housing attaches to an automobile connection point located within the interior of the automobile;
   b. a means for attaching the housing to the automobile connection point wherein the automobile connection point is located within the interior of the automobile and said connection point is capable of attaching to the housing;
   c. the fragrance cartridge, for use with an automobile vent supplying a flow of air, said fragrance cartridge adapted for insertion into the top opening and locking into the cavity of the housing, the fragrance cartridge further comprising a first fragrance cartridge vent disposed on a first side of the fragrance cartridge, and a second fragrance cartridge vent disposed on a second side of the fragrance cartridge, wherein where the fragrance cartridge is properly inserted into the top opening and cavity of the housing, the first housing vent and the first fragrance cartridge vent are in alignment and the second housing vent and the second fragrance cartridge vent are in alignment;

d. a digital signal component, said digital signal component further comprising:

a microprocessor housed within the digital signal component, wherein the microprocessor is configured to process input commands to a digital signal component; the microprocessor operatively connected to an input component, wherein the input component enables the automobile driver to program the digital signal component to signal whether the fuel tank is located on the left or right side of the automobile, the input component coupled to the microprocessor, and a Light Emitting Diode ("LED"), wherein the LED signals whether the fuel tank is located on the right or left side of the automobile, wherein the automobile driver interacts with the input component to program whether the fuel tank is located on the left or right side of the automobile, and wherein the LED signals what side the fuel tank is located wherein the removable fuel tank indicator is universal and removable, and wherein said removable fuel tank indicator signals the automobile driver as to the location of a fuel tank for the automobile, thereby enabling the automobile driver to align the automobile adjacent to the fuel source for efficient and safe refueling of the automobile.

\* \* \* \* \*